United States Patent [19]

Apontoweil et al.

[11] Patent Number: 4,515,777

[45] Date of Patent: * May 7, 1985

[54] VACCINES

[75] Inventors: Peter Apontoweil, Leersum; Manfred M. Krasselt, De Bilt, both of Netherlands

[73] Assignee: Gist-Brocades N.V., Delft, Netherlands

[*] Notice: The portion of the term of this patent subsequent to Jan. 18, 2004 has been disclaimed.

[21] Appl. No.: 440,640

[22] Filed: Nov. 10, 1982

Related U.S. Application Data

[63] Continuation of Ser. No. 103,583, Dec. 14, 1979, abandoned.

[30] Foreign Application Priority Data

Dec. 20, 1978 [NL] Netherlands ............... 78-12359

[51] Int. Cl.$^3$ ................. A61K 39/17; A61K 39/295
[52] U.S. Cl. ........................................................ 424/89
[58] Field of Search ............... 424/88, 89; 435/235, 435/236, 238

[56] References Cited

U.S. PATENT DOCUMENTS

| | | | |
|---|---|---|---|
| 3,060,094 | 10/1962 | Dutcher et al. | 424/89 |
| 3,083,142 | 3/1963 | Howell et al. | 424/89 |
| 3,149,036 | 9/1964 | Woodhour et al. | 424/89 |
| 3,399,263 | 8/1968 | Strazdins et al. | 424/89 |
| 3,678,149 | 7/1972 | Prigal | 424/89 |
| 3,755,557 | 8/1973 | Jacobs | 424/89 |
| 3,876,763 | 4/1975 | Yoshikazu et al. | 424/89 |
| 3,906,092 | 9/1975 | Hilleman et al. | 424/89 |
| 3,983,228 | 9/1976 | Woodhour et al. | 424/89 |
| 4,069,313 | 1/1978 | Woodhour et al. | 424/89 |
| 4,073,743 | 2/1978 | Midler et al. | 424/89 |

FOREIGN PATENT DOCUMENTS

| | | | |
|---|---|---|---|
| 277937 | 11/1965 | Australia | 424/89 |
| 0009277 | 2/1980 | European Pat. Off. | |
| 2382500 | 9/1978 | France | |
| 48-72317 | 9/1973 | Japan | 424/89 |
| 50-6714 | 1/1975 | Japan | 424/89 |
| 52-9727 | 3/1977 | Japan | 424/89 |
| 292949 | 7/1965 | Netherlands | 424/89 |
| 7906696 | 3/1980 | Netherlands | |

OTHER PUBLICATIONS

Cessi, D. et al., Clinica Veterinaria (1975) 98(10):414–417, Prophylaxis of Viral Tenosynovitis of Fowls. Vaccination of Grandparental and Parental Breeding Stock (Ital).
Gough et al., Avian Pathology (1977) 6(2):131–142, Immune Response to Monovalent and Bivalent Newcastle Disease and Infectious Bronchitis Inactivated Vaccines.
Robertson et al., Vet. Rec. 1976 (98):14–15, Field Evaluation of Newcastle Disease Immunisation by Concurrent Inactivated Oil-emulsion and Live B1 Vaccines.
Warden et al., Vet. Bull., 45 (6) #3144 (1975), Immunising Chicks Against Newcastle Disease by Concurrent Inactivated Oil-emulsion and Live B1 Vaccines.
Box et al., Vet. Rec. 1975 96(5):108–111, Newcastle Disease Antibody Levels in Chickens after Vaccination with Oil Emulsion Adjuvant Killed Vaccine.
Levy et al., Vet. Bull. 44 #634 (1974), Immunization of Chickens with an Inactivated Oil-adjuvant Newcastle Disease Virus Vaccine.
Pagnini et al., Vet. Bull. 40 #3949 (1970), Prophylaxis of Newcastle Disease with an Inactivated Vaccine in Oily Adjuvant.
Lombardi, Vet. Bull. 45: 4365 (1975).
van der Heide, L., Vet. Bull. 47th, 2581 (1977).
van der Heide, L., Vet. Bull. 48th, 2261 (1978).

*Primary Examiner*—Shep K. Rose
*Attorney, Agent, or Firm*—Charles A. Muserlian

[57] ABSTRACT

Vaccines derived from aviair reo-virus to combat aberations of the skeleton such as rachitis—like symptoms, diarrhoea and growth inhibition, a process for their preparation as well as combined, inactivated vaccines, ready for administration and active against at least Newcastle disease and aberations of the skeleton, diarrhoea and growth inhibition and process for the preparation of such vaccine. The combined vaccine is prepared by addition of a Newcastle disease virus (NDV) containing liquid obtained by cultivation of a NDV, followed by inactivation of this liquid and optionally homogenizing it, together with a reo-virus containing liquid obtained by cultivation of a reo-virus, followed by inactivation of this liquid and optionally homogenizing it to an oily phase containing as essential components at least one of the components selected from the group consisting of light paraffinic mineral oils, plant oils and naphthenic mineral oils and one or more emulsifiers such as nonionic surface-active compounds derived from alkylene oxide and/or hexahydric alcohols and/or higher natural fatty acids such as esters or ester-ethers, optionally followed by homogenizing and/or addition of a preservative.

5 Claims, No Drawings

VACCINES

PRIOR APPLICATION

This application is a continuation application of U. S. patent application Ser. No. 103,583 filed Dec. 14, 1979, now abandoned.

STATE OF THE ART

It is known that reo-viruses may cause several diseases in poultry such as arthritis/tenosynovitis, myocarditis, hepatitis, hydropericardium, and diseases in the digestive track and/or the respiratory tracks. Avian Pathology, Vol. 6 (1977), pages 271 to 284, for example, gives a survey of various pathogenic microorganisms which may cause by themselves or in combination the viral arthritis/tenosynovitis, such as Staphylococcus, Salmonella, Pasteurella, Erysipelotrix, *Mycobacterium avium, Bacterium arthropyogenes, Escherichia venezuelensis, Streptobacillus monilliformis, Mycoplasma gallisepticum, Mycoplasma synoviae* and reo-viruses, such as the Connecticut reo-virus isolate S 1133, the LZ 671 virus, or the RAM-1 virus, the reo viruses being considered the principal disease inducers. It has been found that viral arthritis/tenosynovitis and other diseases caused by reo-virus infection plays an important part in the cause of considerable economic losses in the poultry farming in many parts of the world.

Furthermore, there has been proposed a method for giving protection against viral arthritis by vaccination during the growth period and the subsequent transfer of maternally produced anti-bodies to the descendants by means of vaccination with reo-virus vaccines. It has been found experimentally in this connection that immunization of breeding animals only protected the first generation descendants, but not the second generation descendants.

It also appears from prior publications, e.g. in Neth. J. Vet. Sci., Vol. 3, No. 1 (1970), pages 5 to 10, that reo-viruses such as the LZ 671 reo-virus are considered to be responsible predominantly for synovitis symptoms in broiler parents. Moreover, Poultry Digest of February 1978, page 102, also discloses that reo-virus may cause growth inhibition and diarrhoea in broilers which may cause growth inhibition by oral infections with digestive suspensions in chickens. Although virus material cultivated in eggs did not cause growth inhibition after oral administration, but caused "pasting", intraperitoneal injection of virus cultivated in eggs caused growth inhibition. The observed disease symptoms are brought into relation with an apparently necessary combination of infectious agents.

On the other hand, more recent publications disclose that the cause of rachitis-like symptoms may be caused by occurrence of toxic compounds produced by molds such as Fusarium moniliforme Sheldon. Zbl. Vet. Med. B. Vol. 25 (1978), pages 29 to 44, discloses for example that rachitis symptoms observed during recent years in various countries in broilers appear to be caused primarily by toxic compounds produced by the above indicated mold, which appeared able to develop in the usual poultry feed in potentialy present spores, preferably under the somewhat moist conditions of the autumn and winter seasons.

Although in the years preceding those in which the published symptoms occured, the observed rachitis symptoms could reasonably be combatted by a vitamin therapy, this therapy did not lead or lead substantially less to improvement of the disease symtoms found later on. It has been tried, therefore, to reproduce the symptoms observed later on by administration of feed selected especially in this connection, and to influence those symptoms by administration of vitamins and/or minerals and to investigate those symptoms more deeply, avoiding as far as possible the occurrence of diseases caused by parasites or microorganisms pathogenic for poultry, such as reo viruses, *Mycoplasma gallisepticum* and *M. synoviae* and other bacteria, by means of processes suitable for that purpose.

It was concluded that, also in view of harmful properties of the metabolism products of especially *Fusarium monoliforme* found in recent years and the mentioned disease symptoms in broilers, there must be a causal connection, despite the fact that no accurate and decisive identification of the metabolites actually responsible therefrom had taken place. From, e.g. Feedstuffs, May 8, 1978, pages 95 and 96, it appears that the actual main cause of those rachitis symptoms has not yet actually been found.

It was, however, suprisingly found that the still to a greater extent occurring aberations in the skelton, such as rachitis-like symptoms, in poultry, especially broilers, often occurring with growth inhibitions and diarrhoea, may be combatted by vaccination of broiler mother animals and their descendants with inactivated vaccines derived from certain aviair reo-viruses. It is known, however, from e.g. Avian Pathology, Vol. 6, page 279 that attempts have been made in the past to inhibit viral arthritis/tenosynovitis in poultry by vaccination with reo-virus vaccines, but it was definitely not obvious for an expert to use reo-virus vaccines to combat, e.g. rachitis-like symptoms which have become more and more serious in recent years in all parts of the world as a problem needing more and more badly an effective and efficient solution.

OBJECTS OF THE INVENTION

It is an object of the invention to provide a novel vaccine derived from aviair reo-virus and to a process for its preparation.

It is another object of the invention to provide a ready for use novel combined, inactivated vaccine from avair reo virus and one or more other viruses e.g. Newcastle disease virus, to a process for its preparation, and to a novel method of preventing Newcastle disease, skeleton aberations, diarrhoea and growth inhibition in poultry.

These and other objects and advantages of the invention will become obvious from the following detailed description.

THE INVENTION

The novel vaccine of the invention is an inactivated vaccine against at least aberations in the skeleton such as rachitis-like symptoms caused by aviair reo viruses alone or in combination with others in poultry.

The vaccination with reo-virus vaccines is preferably applied to broiler chicken female fowl and preferably immediately before the lay of those fowl to avoid the above indicated aberations of the skeleton and the diarrhoea and growth inhibition caused by aviair reo-viruses in broilers due to virus infections through the eggs and, also to protect the descendants against this infection by material immunity transfer during the first weeks after birth.

The vaccines according to the invention may be obtained by preparing a reo-virus-containing liquid by manners known per se, preferably by cultivating a suitable reo virus such as the LZ 671 virus described in detail in the past and a sample of which was deposited with the Collection d'Institut Pasteur Paris under I.092, in an impregnated chicken egg or in an SPF chicken embryo fibro-blast cell culture, by collecting the cultivated virus in a liquid of a suitable titre and by inactivating it, suspending it in a suitably buffered solution and optionally by homogenizing it.

In a preferred process for the preparation of a liquid containing a suitable reo-virus such as the virus strain deposited under I.092 with the Collection d'Institut Pasteur, Paris, the virus is cultivated in a SPF chicken embryo fibro-blast culture, e.g. in a monolayer rolling bottle culture or a culture of cells attached to solid inert carriers, perferably in a monolayer rolling bottle culture.

Preferably, use is made of a cell culture obtained by suspending the starting cells in a culture medium containing at least 85 to 95 parts of Eagle medium with or without 5 to 15 parts of calf serum, an aqueous sodium bicarbonate solution of 2 to 4% and 1 to 5 parts of a solution or suspension of one or more antibiotics such as penicillin G, streptomycin and natamycin whereby the culture medium is separated when the cell culture is nearly closed. The solution of antibiotics contains, e.g. 2 to $3 \times 10^4$ units of penicillin, 20 to 30 mg of streptomycin and 0.4 to 0.8 mg of natamycin per ml.

After inoculation with virus suspension, the culture is incubated at 37° C. for 0.5 to 3 hours to adhere the virus, and maintenance medium consisting of Eagle's maintenance medium with 4 to 6 parts of calf serum, 3 to 6 parts of Tryptose phosphate broth (100 g/l), 10–20 parts of bovine amnion fluid and the additives mentioned herebefore is added, and the virus-containing medium and cells are harvested after 0.5 to 3 days after appearance of the CPE. The cell culture is preferably inoculated with a reo-virus suspension having an activity of $2 \times 10^6$ to $10^8$ TCID 50/rolling culture bottle, preferably $\geq 30 \times 10^6$ TCID 50/rolling culture bottle.

The inactivation of the starting virus liquid may be carried out with the usual inactivators, preferably with β-propiolactone, combined or not combined with a stabilizer, or with formaldehyde, (0.02–0.5%), more particularly by adding β-propiolactone in a concentration of 0.05 to 0.25% by weight (calculated on the aqueous phase weight) to the buffered virus-containing liquid, and by incubating that liquid for 1 to 2 hours, preferably for 90 minutes at about 37° C. Then, the virus liquid is homogenized in the usual way, if necessary. If desired, a preservation compound may be added thereafter to the aqueous phase, such as thiomersal or formaline in a buffered solution.

For the preparation of the vaccine to be administered, actually 300 to 500 ml of an inactivated, optionally homogenized reo-virus-containing liquid is added to 500 to 700 ml of an oily phase. The essential components of the oily phase are at least one of the components selected from the group consisting of light paraffinic mineral oils (FDA quality), plant oils and naphthenic mineral oils, and one or more suitable emulsifiers in the form of nonionic surfaceactive compounds derived from alkylene oxide and/or hexahydric alcohols and/or higher natural fatty acids of 10 to 20 carbon atoms, such as esters and ester-ethers. Examples thereof are mannide monooleate (Span 80 and Arlacel A) and polyoxyethylene (20) sorbitan monooleate (e.g. Tween 80).

The volume ratio of the aqueous phase, formed by the virus liquid, and the oily phase may vary from 1:1 to 3:7 and is preferably about 7:13. It has been found that the aqueous phase must be added to the oily phase under vigorous stirring and/or homogenization to obtain the desired stable thin-liquid final emulsion. The oily phase contains 2 to 20% by weight (calculated on the oily phase weight) of emulsifier, preferably 2 to 15% by weight of Arlacel A or Arlacel 80 or Span 80 and 0.2 to 4% of Tween 80. The components of the oily phase are preferably heated separately in an autoclave to at least 110° C. or sterile filtered as a mixture.

The invention also includes inactivated virus vaccines derived from at least a reo-virus-containing liquid, i.e. inactivated sole vaccines derived from reo-viruses as well as combined inactivated vaccines ready for use and derived from reo-virus and one or more other viruses. Such combined inactivated vaccines are to be used against various diseases which may be caused by reo-virus themselves, such as viral arthritis/tenosynovitis, myocarditis, hepatitis, hydropericardium, diseases in the digestive tract and/or respiratory track, aberations of the skeleton such as rachitis-like symptoms, diarrhoea and growth inhibition, and diseases mainly attributed to the action of other virus types, e.g. Newcastle disease.

It will be known to every expert that disease symptoms may often by caused by combinations of occurring virus types. In connection therewith, poultry are for practical reasons, simultaneously or shortly after each other vaccinated with two or more virus vaccines against the most frequently occurring virus diseases. The hitherto usual method consisted of mixing standard volumes of different vaccines ready for use, and administering the so prepared vaccine does on the spot which thus generally consisted of twice the volume of the vaccines to be applied separately. In addition, an accurate mixing cannot be or can hardly be guaranteed and problems may arise due to foreign infective compounds. Therefore it was aimed to provide an improved combined, ready for use vaccine giving sufficient protection against Newcastle disease as well as against one or more of the diseases caused by reo virus, such as viral arthritis/tenosynovitis, myocarditis, hepatitis, hydropercardium, diseases in the digestive track and/or respiratory track, aberations of the skeleton, such as rachitis like symptoms, diarrhoea and growth inhibition.

Therefore the invention also relates to combined inactivated vaccines against Newcastle disease (ND) and reo-virus infections derived from NDV and reo-virus-containing liquids. The Newcastle disease is still one of the most important respiration diseases in poultry and may cause a high rate of mortality in poultry of all ages, especially young broilers.

Various vaccines have been developed against Newcastle disease, and it turned out that these vaccines are perferably administered in the inactivated form, since that form provides a high rate of safety and results in high humoral anti-body titres, especially with revaccinations. In addition, the use of live vaccine sometimes caused distribution of the inoculation virus from vaccinated poultry to poultry susceptible to infections or not being immune.

Although various relatively safe and good immunizing live ND vaccines have been developed in the meantime, as appears from British Patent No. 1,510,100, there is still a clear need for inactivated ND vaccines. Combined inactivated vaccines against respiratory diseases in poultry characterized by the combination of a dead vaccine against infectious coryza, obtained by cultivating a *Haemophilus gallinarum* strain in a natural nutrient medium and by inactivating the bacteria, with a dead vaccine of an infectious bronchitis virus and a dead ND vaccine are known, e.g. from Dutch published Patent Application No. 7117873 (published for opposition purposes under No. 157209). U. S. Pat. No. 2,798,835 discloses combined vaccines consisting of a combination of a vaccine against infectious bronchitis and an ND vaccine, both components being derived from live viruses.

According to the process for the preparation of the combined vaccines of the invention, an inactivated NDV-containing liquid is prepared in a manner known per se, e.g. by cultivating the desired virus in an impregnated chicken egg, collecting the cultivated virus in a liquid of a titre usual for this kind of vaccine and inactivating, suspending the virus in a suitable buffered solution and/or homogenizing, and mixing with an inactivated reo virus liquid obtained by cultivating the virus by methods described hereinbefore, collecting the formed virus in a liquid of a titre usable for this type of vaccine and inactivating the virus liquid by methods known per se.

For the preparation of NDV-containing liquid various slightly virulent or practically avirulent, lentogenic or velogenic ND viruses having good immunizing properties may be used, such as the La Sota or Hitchner 30 virus (lentogenic) or the Herts 33/56 virus (velogenic). Specific examples of applicable virus strains are the strains P/76/5, P/76/4 and P/76/3 obtainable from Institut fur Medizinische Mikroboiologie, Infections and Seuchenmedizin der Ludwig Maximilians Universitat, Munchen, the VR-108, VR-107, VR-109, VR-699, VR-623 strains obtainable from the American Type Culture Collection, Rockville, Maryland USA, the Queensland V4 strain, obtainable from the Centr. Vet. Lab., Weybridge, Great Britian, or the LZ258P virus deposited with the Collection d'Institut Pasteur, Paris under No. I-091.

For the preparation of the combined vaccines, 150 to 250 ml of an NDV-containing liquid is inactivated, then is optionally homogenized and, together with 100 to 250 ml of the reo-virus-containing liquid being inactivated and optionally homogenized first, is added to 500 to 700 ml of an oily phase of the composition mentioned hereinbefore. The starting virus containing liquids have preferably been buffered. The volume ratio of the NDV-containing liquid and the reo-virus-containing liquid may vary from 3:4 to 5:1 and is preferably about 3:2.

The volume ratio of the aqueous phase formed by both virus liquids and the oily phase may vary from 1:1 and 3:7, and is preferably about 7:13. It has been found that the aqueous phase must be added to the oily phase with vigorous stirring and/or homogenizing to obtain the desired stable and thin-liquid final emulsion. The oily phase contains 2 to 20% by weight (calculated on the oily phase weight) of an emulsifier, and contains preferably 2 to 15% by weight of Arlacel A or Arlacel 80 or Span 80 and 0.2 to 4% of Tween 80. The components of the oily phase are preferably heated to at least 110° C. in an autoclave separately or sterile filtered as a mixture.

The inactivation of both starting virus liquid components may be carried out with the usual inactivators, e.g. by means of β-propiolactone optionally combined with a stabilizer or formaldehyde. Preferably, β-propiolactone is added in a concentration of 0.05 to 0.25% by weight (calculated on the aqueous phase) to a buffered ND virus-containing liquid and the liquid is incubated at 37° C. for 1 to 2 hours, preferably for 90 minutes, while the buffered reo-virus liquid is also inactivated with β-propiolactone optionally combined with a stabilizer in a concentration of 0.05–0.25% by weight at 37° C. for 1 to 2 hours. Then, the virus liquids are homogenized in the usual way, if necessary. A preservative such as thiomersal or formaline in a buffered solution may be added to the aqueous phase.

For obtaining suitable combination vaccines with the desired good properties, a NDV liquid having a titre of $10^{9.8}$ to $10^{10.5}$ EID 50/ml, preferably $\geq 10^{10}$ EID 50/ml and a reo virus liquid with a titre of $10^{5.5}$ to $10^{7.5}$ EID 50/ml, preferably $> 10^{6.0}$ EID 50/ml must be used. The vaccines prepared in this way are preferably administered to 1 to 30 weeks old, preferably 10 to 20 weeks old, broiler parent animals before their lay.

In the following examples there are described several preferred embodiments to illustrate the invention. However, it is to be understood that the invention is not intended to be limited to the specific embodiments.

EXAMPLE 1

Preparation of reo-virus vaccine (a) Culture of Reo-virus

SPF eggs brooded for 10 days were inoculated with LZ 671 seed virus and after incubation at 37° C. for 76 hours, the AAL (amnion allantoic liquid) was harvested. The AAL contained then about $10^{6.0}$ EID 50/ml. The virus suspension was frozen at −20° C. and was stored for vaccine production.

(b) Treatment of virus suspension

The frozen virus suspension was defrosted and inactivated in a water bath with 0.05 to 0.25% β-propiolactone at 37° C. for 90 minutes and the suspension was held overnight at +4° C. The inactivation was controlled by observation of the formation of CPE's on CEF followed by a hemabsorption test. Moreover, previously brooded SPF chicken eggs were incubated with the inactivated virus fluid and were subsequently controlled. The virus suspensions were homogenized with an Ultra Turrax homogenizer and the emulsion was optionally diluted with PBS +0.3% of formaline, depending on the $TCID_{50}$ or the $EID_{50}$ of the AAF and the titre of the reo-virus suspension. The NDV-AAL and the reo-virus suspension were mixed thereafter in a ratio of 6:4 and used for emulsion preparation.

(c) Preparation of emulsion

The virus suspension was injected in an oily phase at room temperature while simultaneously homogenizing with the Ultra Turrax homogenizer. The addition of the aqueous phase was stopped when the ratio of 6:5 parts of oil to 3:5 parts of virus suspension was reached. Homogenizing was continued until the drop-size of the aqueous phase was about 0.05–0.5 μm. The oily phase used had the following composition:

Marcol 52 (white paraffinic Esso oil)—93.6%

Arlacel A or Arlacel 80 or Span 80 (mannide monooleate)—6.0%

Tween 80 (polyoxyethylene 20 sorbitan monooleate)—0.4%

The compounds of the oily phase were separately heated to 110° C. in the autoclave or sterile filtered as a mixture. That a stable emulsion was obtained was determined by (1) pipetting drops directly after emulsifying onto a water surface, whereby the drops did not spread, but remained intact; and (2) storage at 37° C. for 4 weeks without formation of any aqueous phase. The final concentrations of the thus prepared emulsion were 21% NDV containing buffered liquid and 14% reo virus containing buffered liquid and the vaccine obtained could be used in a dosage of 0.5 ml per animal intramuscularly in the breast or leg muscles or subcutaneously in the neck.

EXAMPLE 2

Preparation of combined reo-virus/NDV vaccine (a) Culture of reo-virus (strain LZ 671)

Cell cultures were prepared from chicken eggs brooded for 10 days in (Bellco) rolling culture bottles starting from CEF in Eagle medium with 10% of newborn calf serum containing 0.22% by weight of sodium bicarbonate and 2 volume-% of an antibiotic solution containing per ml $25 \times 10^3$ units of penicillin G, 25 mg of streptomycin and 0.6 mg of natamycin. The medium was vaccum filtered when the cell cultures were nearly closed and then the cultures were inoculated with LZ 671 virus suspension and filled up with Eagle maintenance medium containing 4 volume-% of calf serum, 4 volume-% of Tryptose phosphate broth (100 g/l) 15% bovine amnion fluid, 0.22% by weight of $NaHCO_3$ and 3% of the above mentioned antibiotic solution. The reo-virus-containing medium with the cells was harvested 1 day after appearance of CPE's. The virus suspension was frozen at $-20°$ C. and was stored for vaccine production. A $TCID_{50}$ of this suspension was determined.

(b) Cultivation of NDV

SPF eggs brooded for 11 days were inoculated with LZ 258P seed virus and after incubation at 37° C. for 72 hours, the AAF was harvested. The AAF contained then about $10^{10}$ EID 50/ml. The virus suspension was frozen at $-20°$ C. or lower and was stored for vaccine production.

(c) Treatment of virus suspension

The frozen virus suspensions were defrosted and inactivated in a water bath with 0.05 to 0.25% of $\beta$-propiolactone at 37° C. for 90 minutes and the suspensions were held overnight at $+4°$ C. The inactivation was controlled by testing the formation of CPE's on CEF or EID 50-test for the reo virus and EID 50-test for the NDV. The virus suspensions were homogenized with an Ultra Turrax homogenizer and the suspension was optionally diluted with PBS $+0.3\%$ of formaline depending on $TCID_{50}$ or $EID_{50}$. The suspensions of the NDV and the reo-virus were then mixed in a ratio of 6:4 and were used for preparation of the emulsion.

(d) Preparation of the emulsion

The mixed virus suspension was injected into the oily phase at room temperature, while simultaneously homogenizing with the Ultra Turrax homogenizer. The addition of the aqueous phase was stopped when the ratio of 6.5 parts of oil to 3.5 parts of virus suspension was reached and honogenizing was continued until the drop-size of the aqueous phase was about 0.05-0.5 µm. The oily phase used had the following composition:

Marcol 52 (white paraffinic Esso oil)—93.6%
Arlacel A or Arlacel 80 or Span 80 (mannide monooleate)—6.0%
Tween 80 (polyoxyethylene 20 sorbitan monooleate)—0.4%

The components of the oily phase were heated separately to 110° C. in an autoclave or sterile filtered as a mixture. The final concentrations of the thus prepared emulsion were 21% NDV containing buffered liquid and 14% reo-virus containing buffered liquid. The vaccine obtained was used in a dosage of 0.5 ml per animal intramuscularly in the breast or leg muscles or subcutaneously in the neck. Ten days after vaccination, antibodies were detectable by the immuno diffusion test.

EXAMPLE 3

Preparation of combined reo/NDV vaccine (a) A reo containing liquid was prepared by the corresponding step of Example 1 and the virus suspension was inactivated with 0.02-0.5% formaldehyde for 20 hours at 22° C. and then homogenized with an Ultra Turrax homogenizer.

(b) A NDV containing liquid was prepared by the corresponding step of Example 2 and the treatment of the NDV suspension was carried out in the same way as in Example 2.

(c) The treated NDV-AAF and reo-AAF were mixed thereafter in a proportion of 5:4.

(d) The combined virus suspensions were added to and mixed with an oily phase in the proportion of 6 parts of oily phase: 4 parts of virus containing liquid and an emulsion was prepared passing it through a colloid mill. The applied oily phase had the following composition:

Marcol 52 (white paraffinic Esso oil)—91.4 vol %
Arlacel A or Arlacel 80 or Span 80 (mannide monooleate)—8.0 vol %
Tween 80 (polyoxylethylene 20 sorbitan monooleate)—0.6 vol %

Various modifications of the vaccine and the methods of the invention may be made without departing from the spirit or scope thereof and it is to be understood that the invention is intended to be limited only as defined in the appended claims.

We claim:

1. In a combined inactivated vaccine ready for use against symptoms in poultry caused by avian reo viruses and by Newcastle disease virus (NDV), characterized in that the vaccine contains an inactivated Newcastle disease virus containing liquid having a titre of $10^{9.8}$ $-10^{10.5}$ $EID_{50}$/ml, and an inactivated reo virus containing liquid derived from reo virus strain LZ 671 deposited with Collection d'Institut Pasteur, Paris under No. 1.092 having a titre of $10^{5.5}$ $-10^{7.5}$ $EID_{50}$/ml, the improvement consisting essentially of the volume ratio between the Newcastle disease virus containing liquid and the reo virus containing liquid being from 3:4 to 5:1, and wherein an oil phase with essential components selected from the group consisting of at least light paraffinic mineral oils (FDA quality), plant oils and naphthenic mineral oils and at least one emulsifier in the form of non-ionic surface-active compounds derived from esters or esterethers of alkylene oxide and/or hexahydric alcohols and/or higher natural fatty acids of 10 to 20 carbon atoms, the volume ratio between the aqueous phase formed by both virus liquids and the oil phase being from 7:13 to 3:7.

2. Inactivated vaccine of claim 1 wherein the oily phase contains 2 to 20% by weight of an emulsifier calculated on the oily phase weight.

3. The vaccine of claim 2 wherein the emulsifier is 2 to 15% by weight of Arlacel A or Arlacel 80 or Span 80 or 0.2 to 4% of Tween 80.

4. The combined vaccine of claim 1 wherein the ratio is about 3:2.

5. Process for preventing symptoms caused by Newcastle disease and by aviair reo-virus in poultry comprising vaccinating the poultry with the vaccine of claim 1.

* * * * *